United States Patent
Swift et al.

(10) Patent No.: US 11,896,507 B2
(45) Date of Patent: Feb. 13, 2024

(54) SELF EXPANDING STENT AND METHOD OF LOADING SAME INTO A CATHETER

(71) Applicant: Cook Medical Technologies LLC, Bloomington, IN (US)

(72) Inventors: Richard A Swift, South Bend, IN (US); Sam C Mullins, Limerick (IE); Stephen T Clancy, Clare (IE)

(73) Assignee: Cook Medical Technologies LLC

( * ) Notice: Subject to any disclaimer, the term of this patent is extended or adjusted under 35 U.S.C. 154(b) by 46 days.

(21) Appl. No.: 17/713,399

(22) Filed: Apr. 5, 2022

(65) Prior Publication Data

US 2022/0370215 A1 Nov. 24, 2022

Related U.S. Application Data

(60) Provisional application No. 63/190,906, filed on May 20, 2021.

(51) Int. Cl.
*A61F 2/88* (2006.01)
*A61F 2/844* (2013.01)
(Continued)

(52) U.S. Cl.
CPC .............. *A61F 2/88* (2013.01); *A61F 2/844* (2013.01); *A61F 2/91* (2013.01); *A61F 2/966* (2013.01);
(Continued)

(58) Field of Classification Search
CPC .... A61F 2/88; A61F 2/844; A61F 2230/0039; A61F 2230/0052; A61F 2/915; A61F 2250/0036; A61F 2250/0037
(Continued)

(56) References Cited

U.S. PATENT DOCUMENTS 6,231,598 B1    5/2001    Berry et al.
6,464,720 B2 *  10/2002   Boatman ................ A61F 2/915
                                                              623/1.34
(Continued)

FOREIGN PATENT DOCUMENTS

EP    1236445 A2 *   9/2002   ............... A61F 2/91
EP    1917931       5/2008
EP    3281668 A1 *  2/2018   ............. A61F 2/844

OTHER PUBLICATIONS

European Patent Office, International Search Report, PCT/US2022/023012, dated Jun. 17, 2022, 12 pages, European Patent Ofice, NL-2280 HV Rijswijk, Netherlands.
(Continued)

*Primary Examiner* — Tan-Uyen T Ho
*Assistant Examiner* — Osama Nemer
(74) *Attorney, Agent, or Firm* — Woodard, Emhardt, Henry, Reeves & Wagner, LLP

(57) ABSTRACT

A stent comprises a framework that includes a sequence of cells that each occupy a discrete segment of the stent length, and each of the cells includes a plurality of struts with ends connected at respective vertices. An adjacent pair of the cells are attached to one another by a plurality of T-bars that each include a column defining a long axis that extends parallel to the stent axis, and a top bar attached to one end of the column. An opposite end of the column is attached to a first cell, and the top bar is attached at opposite ends to a second cell of the adjacent pair of cells. The column has a minimum width perpendicular to the long axis that is wider than a maximum width of each of the struts, and the column defines at least one slot. The top bar includes a curved edge on an opposite side from the column, and the curved edge straddles the long axis.

18 Claims, 4 Drawing Sheets

(51) Int. Cl.
  *A61F 2/91* (2013.01)
  *A61F 2/966* (2013.01)
  *A61F 2/915* (2013.01)

(52) U.S. Cl.
  CPC .............. *A61F 2002/91558* (2013.01); *A61F 2002/91566* (2013.01); *A61F 2210/0014* (2013.01); *A61F 2230/0039* (2013.01); *A61F 2230/0052* (2013.01)

(58) Field of Classification Search
  USPC ................................................ 623/1.34, 1.15
  See application file for complete search history.

(56) References Cited

U.S. PATENT DOCUMENTS

| | | | |
|---|---|---|---|
| 6,558,415 B2* | 5/2003 | Thompson | A61F 2/915 623/1.15 |
| 6,827,732 B2* | 12/2004 | Thompson | A61F 2/915 623/1.15 |
| 7,381,217 B2 | 6/2008 | Tischler | |
| 9,381,103 B2* | 7/2016 | Abunassar | A61F 2/915 |
| 9,498,360 B2* | 11/2016 | Layman | A61F 2/89 |
| 10,004,623 B2* | 6/2018 | Dorn | A61F 2/82 |
| 10,849,769 B2* | 12/2020 | Harrison | A61F 2/9522 |
| 11,628,077 B2* | 4/2023 | Ramzipoor | A61F 2/945 264/308 |
| 2001/0027339 A1 | 4/2001 | Boatman et al. | |
| 2002/0120322 A1* | 8/2002 | Thompson | A61F 2/91 623/1.11 |
| 2006/0025847 A1 | 2/2006 | Parker | |
| 2006/0271170 A1* | 11/2006 | Gale | A61F 2/915 623/1.49 |
| 2008/0255655 A1* | 10/2008 | Kusleika | A61F 2/91 623/1.11 |
| 2008/0294238 A1 | 11/2008 | Tischler et al. | |
| 2009/0204200 A1 | 8/2009 | Bales, Jr. et al. | |
| 2009/0240318 A1* | 9/2009 | Chalekian | A61F 2/856 623/1.35 |
| 2010/0004735 A1 | 1/2010 | Yang et al. | |
| 2010/0114296 A1 | 5/2010 | Case et al. | |
| 2010/0292778 A1* | 11/2010 | Roeder | A61F 2/91 623/1.17 |
| 2012/0215298 A1* | 8/2012 | Hansen | A61F 2/915 623/1.13 |
| 2013/0073052 A1* | 3/2013 | Kim | A61F 2/915 623/23.7 |
| 2013/0123905 A1* | 5/2013 | Abunassar | A61F 2/89 623/1.16 |
| 2013/0197617 A1* | 8/2013 | Armstrong | A61F 2/90 623/1.2 |
| 2016/0120671 A1* | 5/2016 | Higashi | A61F 2/90 623/1.34 |
| 2018/0140444 A1* | 5/2018 | Neuss | A61F 2/915 |
| 2018/0360630 A1* | 12/2018 | Kim | A61F 2/915 |
| 2021/0077283 A1* | 3/2021 | Yeh | A61F 2/86 |

OTHER PUBLICATIONS

International Application No. PCT/US2022/023012 International Search Report and Written Opinion, dated Jun. 17, 2022.

* cited by examiner

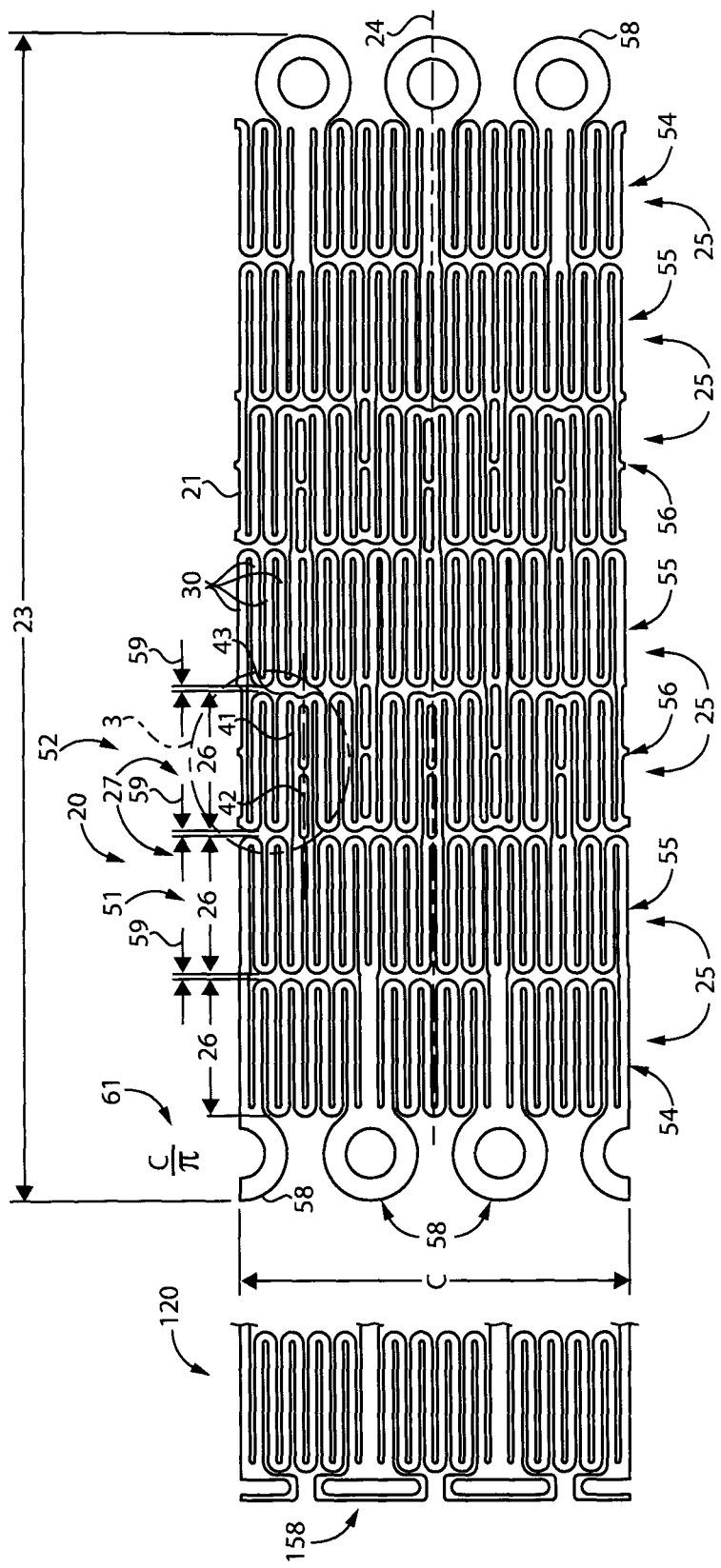

US 11,896,507 B2

1

SELF EXPANDING STENT AND METHOD OF LOADING SAME INTO A CATHETER

TECHNICAL FIELD

The present disclosure relates generally to stents, and more particularly to stent structure that improves load ability into a stent delivery system.

BACKGROUND

One class of self expanding stents are typically cut from a thin walled nitinol tube. Such a stent is shown, for instance in co-owned U.S. Patent publication 2013/0073052. After being cut, the stent is expanded and heat set to a diameter several times larger than the original tube diameter. With the stent now biased toward the larger diameter, the stent is compressed and loaded into a catheter of a stent delivery system. During the loading procedure, the stent is simultaneously circumferentially compressed and longitudinally compressed in order to push the stent into the catheter of the stent delivery system. Because these stents are cut from relatively thin walled nitinol tubes, there is a risk of substantial deformation and maybe even collapse during the loading procedure. As the industry seeks to manufacture ever smaller diameter stents from thinner walled tubes, problems associated with effective loading of the stent into a delivery system can become acute.

The present disclosure is directed toward one or more of the problems set forth above.

SUMMARY

In one aspect, a stent includes a framework with a hollow cylindrical shape having a length along a stent axis. The framework includes a sequence of cells that each occupy a discrete segment of the stent length, and each of the cells includes a plurality of struts with ends connected at respective vertices. An adjacent pair of the cells are attached to one another by a plurality of T-bars that each include a column defining a long axis extending parallel to the stent axis, and a top bar attached to one end of the column. An opposite end of the column is attached to a first cell, and the top bar is attached at opposite ends to a second cell of the adjacent pair of cells. The column has a minimum width perpendicular to the long axis that is wider than a maximum width of each of the struts, and the column defines at least one slot. The top bar has a curved edge on a side opposite from the column, and the curved edge straddles the long axis.

In another aspect, a method of loading a self expanding stent into a catheter of a stent delivery system includes putting the stent into a loading configuration, which includes simultaneously compressing the self expanding stent circumferentially and longitudinally while sliding the stent into the catheter. Adjacent cells of the self expanding stent move from out of contact into contact responsive to the longitudinal compression.

BRIEF DESCRIPTION OF THE DRAWINGS

FIG. 1 is a flat plan view of a stent at a tube diameter according to the present disclosure;

FIG. 2 is a partial flat plan view of an alternative end structure for a stent according to the present disclosure;

2

Figure 5:
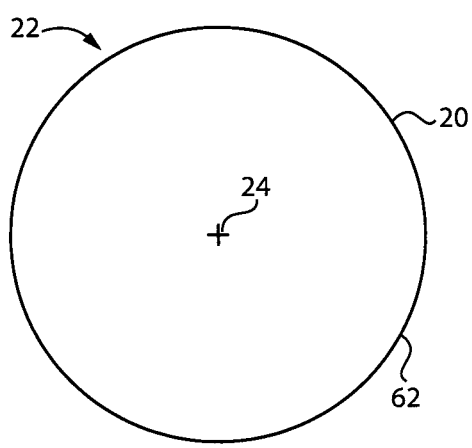
Figure 6:
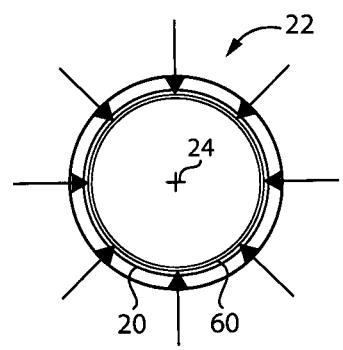
Figure 7:
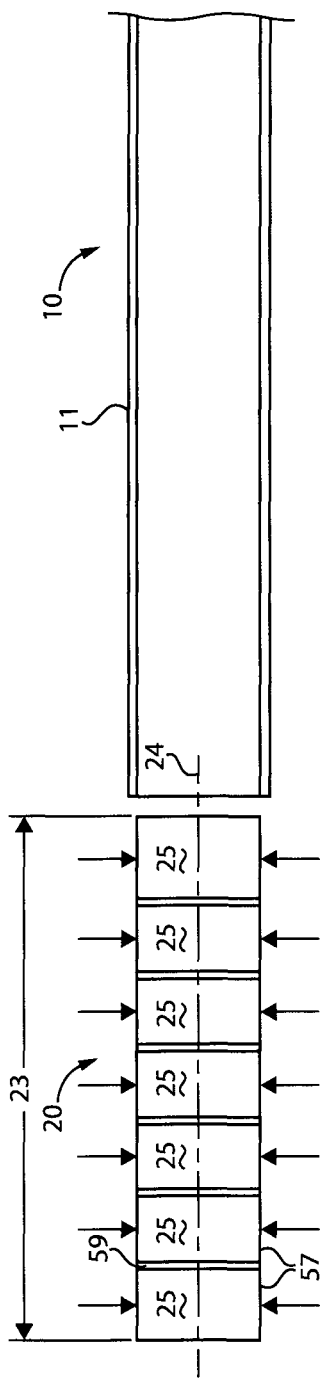
Figure 8:
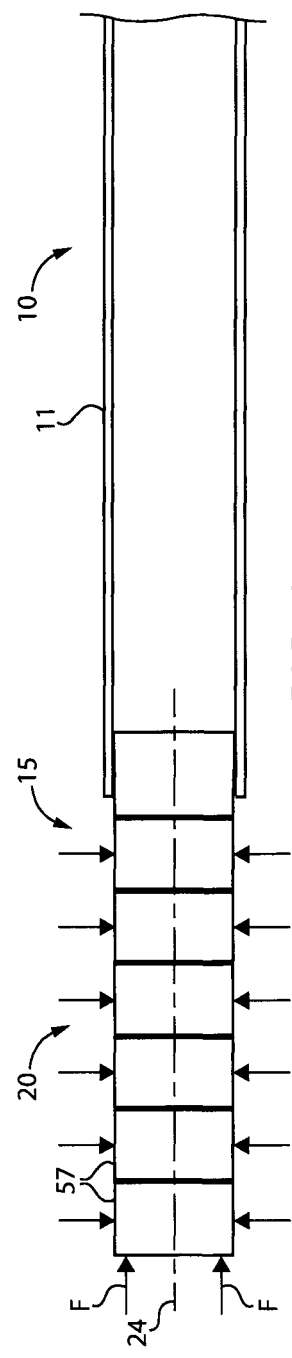
Figure 9:
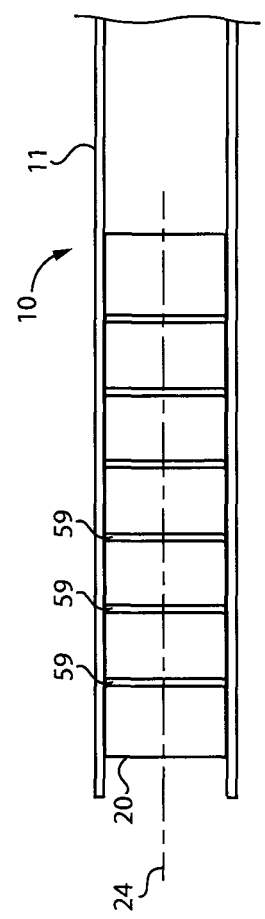

FIG. 5 is an end view of the stent of FIG. 1 showing its hollow cylindrical shape in its expanded diameter;

FIG. 6 is an end view of the stent of FIG. 1 being circumferentially compressed prior to being loaded into a catheter;

FIG. 7 is a side view of the circumferentially compressed stent preparing to be loaded into a catheter;

FIG. 8 is a side view of the stent in a loading configuration partially loaded in the catheter; and FIG. 9 shows the stent after being loaded into the catheter.

DETAILED DESCRIPTION

Figure 3:
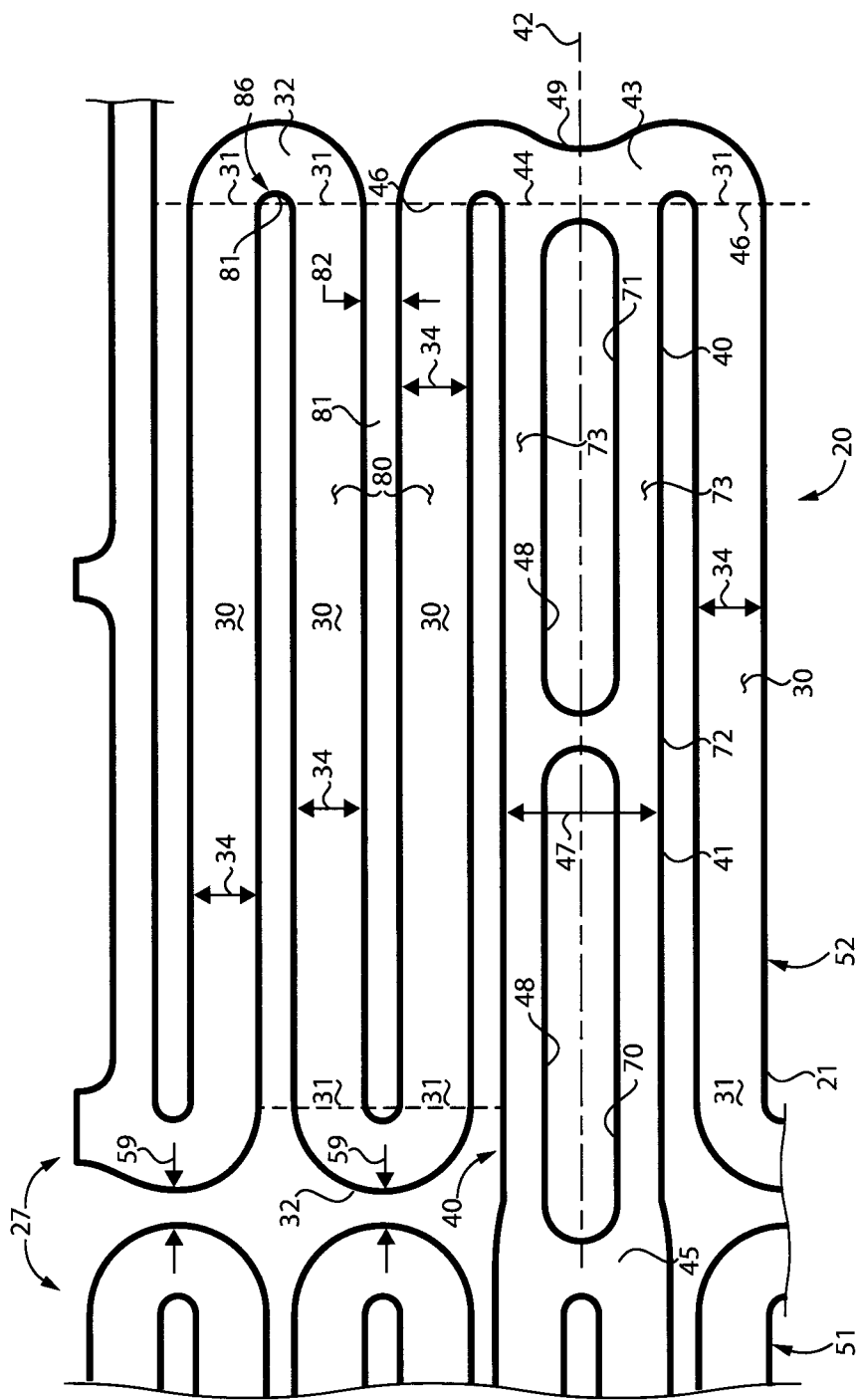
FIG. 3 is an enlarged view of the area 3 shown in FIG. 1.

Referring initially to FIGS. 1 and 3, a stent 20 includes a framework 21 having a hollow cylindrical shape shown in a flat plan view with a length 23 along a stent axis 24. The framework 21 includes a sequence of cells 25 that each occupy a discrete segment 26 of the stent length 23. Each of the cells 25 include a plurality of struts 30 with ends 31 connected at respective vertices 32. Preferably, stent 20 is manufactured from a thin walled metallic tube with material laser cut away to render the pattern shown in FIG. 1. For instance, the example stent 20 illustrated might begin as a nitinol tube with an outer tube diameter of 1.35 millimeters and a wall thickness of 0.12 millimeters. The illustrated embodiment shows a stent 20 with a sequence of seven cells 25, with each adjacent pair of cells 27 being separated by a cell separation distance 59, which may be about equal to a cutting width of the laser used to cut stent 20 from the nitinol tube. As used in the present disclosure, the term "about equal" means that when a ratio of the two quantities is rounded to an integer, that integer is one. In this specific example, the laser cutting width and the cell separation distance 59 are 0.05 millimeters.

An adjacent pair of the cells 27 are attached to one another by a plurality of T-bars 40 that each include a column 41 attached at one end 44 to a top bar 43. The column 41 defines a long axis 42 that extends parallel to the stent axis 24. An opposite end 45 of the column 41 is attached to a first cell 51 of the adjacent pair cells 27, and the top bar 43 is attached at opposite ends 46 to a second cell 52 of the adjacent pair of cells 27. The column 41 has a minimum width 47 perpendicular to the long axis 42 that is wider than a maximum width 34 of each of the struts 30, and the column defines at least one slot 48. In the illustrated embodiment, each column 41 defines exactly two slots 70 and 71 that each are equally sized, share a common centerline and have long dimensions extending along long axis 42. The top bar 43 has a curved edge 49 located on an opposite side from column 41. The curved edge 49 may be a concave edge 49 that faces away from the column 41 and straddles the long axis 42. The curvature of curved edge 49 means that the edge surface bound by the inner and outer tube surfaces has portions on both sides of a plane perpendicular to stent axis 24.

Figure 4:
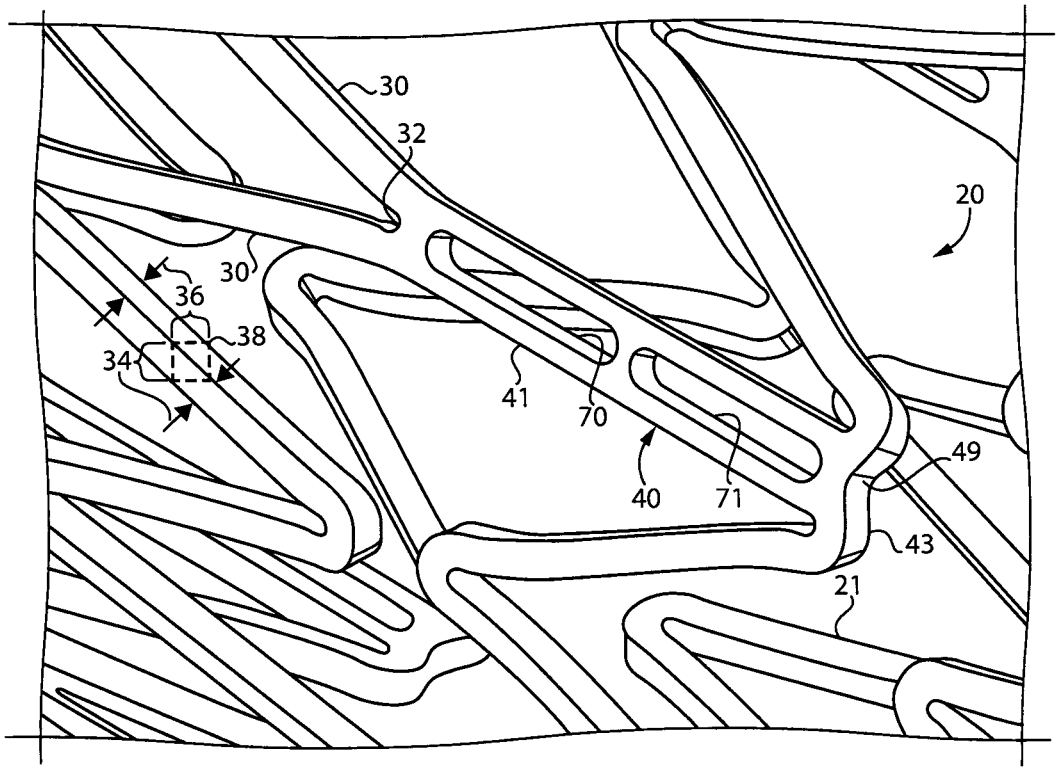
FIG. 4 is a partial view of the stent of FIG. 1 shown in an expanded diameter.

Referring in addition to FIGS. 4 and 5, after the metallic tube is cut into a stent 20 as shown in FIG. 1, the hollow cylindrical shape 22 is expanded to an expanded diameter 62, which in this case may be 4 millimeters, and then heat set at that expanded diameter 62. The result being that the framework 21 is now biased toward the expanded diameter 62. Thus, during manufacture, the stent 20 starts out at a tube diameter 61 (circumference C/Π) that is smaller than an expanded diameter 62 at which the stent is heat set. Later, the stent 20 is then compressed to a loading diameter 60, which is smaller than the tube diameter 61, for loading into a stent delivery system. Although the advanced T-bar structure and geometry of the present disclosure could scale to virtually any sized stent, the present disclosure and the illustrated embodiment is taught in the context of a stent 20 having a tube diameter 61 of five French or less.

In order to provide more longitudinal support when the stent 20 is loaded into a stent delivery system, every strut 30 of the framework 21 may be oriented parallel to the stent axis 24 when the hollow cylindrical shape 22 is at the tube diameter 61, as shown in FIG. 1. As per the illustrated embodiment, each of the struts 30 may have a uniform width 34, a uniform thickness 36 (i.e., the wall thickness of the pre-cut tube) and a rectangular cross section 38. The ratio 37 of the strut width 34 to the strut thickness 36 may be about equal to one. Each adjacent pair of struts 80 may be separated by a rectangular space 81 with a width 82 that is less than a width 34 of each of the adjacent pair of struts 30 when the hollow cylindrical shape 22 is at the tube diameter 61. Although not necessary, the width 82 of the rectangular space 81 may be equal to the width of the laser used to cut stent 20 from the metallic tube, as discussed earlier. Each of the vertices 32 that connect adjacent struts 30, may define a continuous inner curve 85 with a radius 86 the is less than one half of a width 34 of the struts 30 joined by the respective vertex 32. The column 41 of the T-bars 40 may have a tall H shape 72, with each leg 73 of the H shape 72 being less than a width 34 of each of the struts 30. In the illustrated embodiment, the top bar 43 is shown as having a concave edge 49 that faces away from the column 41 and straddles long axis 42. The present disclosure contemplates any curved edge, including convex, on a side of the T-bar that is opposite from the column 41.

Although a stent 20 according to the present disclosure can include any number of cells 25, the illustrated embodiment shows a stent 20 with a sequence of seven cells 25 that include an end cell 54 on each end, a flex cell 55 immediately adjacent each of the end cells 54 and two hoop cells 56, with a single flex cell 55 positioned between the two hoop cells 56. Although the end cells 54 could conceivably utilize the T-bar structure taught in this disclosure for connection to an adjacent cell 25, the adjacent pair of cells 27 that are connected by T-bars 40 according to the illustrated embodiment includes exactly one flex cell 55 and exactly one hoop cell 56. Although not necessary, the frame work 21 can terminate in a plurality of eyelets 58. These eyelets could be omitted without departing from the scope of the present disclosure. Preferably, and especially in the context of smaller diameter stents such as 5 French or less, the framework 21 may terminate in exactly three eyelets 58. FIG. 2 shows an alternative stent structure 120 with rectangular shaped eyelets 158 that also fall within the intended scope of this disclosure.

The T-bar 40 structure and geometry of the present disclosure are believed, along with the other features of stent 20, to maintain good stent performance requirements without undermining the ability of the stent to be loaded into a deliver system. Loading involves compressing the stent 20 down below its tube diameter to a loading diameter, and then pushing the stent out of a compression head and into a delivery system. The reason that loading can be challenging is because the stents are designed to have high radial stiffness in order to help maintain vessel patency after deployment, while maintaining substantial flexibility in other modes of deformation (axial, bending and torsion) in order to achieve good fatigue performance in the body. The present disclosure recognizes that one area of stent geometry that can strongly influence packing density and hence loadability without negative consequences to other stent performance aspects are the geometry and structure of the T-bars 40. The present disclosure recognizes that the width 47 of the column 41 and width of the top bar 43 can be made wider without compromising stent performance in other areas. The T-bars 40 of the present disclosure can also utilize material removal via at least one slot along their long axis 42 centerlines to improve circumferential bending performance that benefits certain stages of stent manufacturing. Specifically, during the manufacture of stents 20, fractures and cracks can occur in the region where the struts 30 merge with the top bar 43 of the T-bars 40. This stress can be caused by the high circumferential stiffness of a wide T-bar. By removing material from the central region of the top bar 43, which is shown in the illustrated embodiment by the concave edge 49, adequate circumferential stiffness is alleviated to allow small diameter thin walled stents to be manufactured and undergo expansion and heat-setting operations without cracking. Thus, an alternative to the concave edge 49 shown could be to have that surface of the top bar 43 be made convex instead, and material removal according to the teaching of the present disclosure to address circumferential stiffness could be achieved by possibly extending the length of slot 71 along long axis 42 to reduce the amount of material that makes up top bar 43.

Referring now in addition to FIGS. 7-9, a loading procedure for a stent 20 according to the present disclosure is schematically illustrated. The loading procedure begins by circumferentially compressing the stent down to a loading diameter 60 that is smaller than the tube diameter 61. For instance, in one specific example, the tube diameter could be 1.35 millimeters for a 5 French stent, and the corresponding loading diameter might be 1.34 millimeters. The circumferentially compressed stent is then moved toward loading into a catheter 11 of a stent delivery system 10 as shown in FIG. 7 with a device identified as a compression head. Next, a force F is applied to push the stent 20 into catheter 11 while maintaining the circumferential compression. The result of this is to put stent 20 into a loading configuration 15 in which the stent is simultaneously compressed circumferentially and longitudinally while the stent 20 is slid into the catheter 11. This longitudinal stress may cause adjacent cells 25 to move from out of contact into contact responsive to the longitudinal compression. This contact between adjacent cells 25 is believed to provide additional column strength and longitudinal rigidity to the stent 20 while being loaded to avoid undesirable outcomes, such as buckling or other undesirable deformations during the loading process. The longitudinal compression on stent 20 during the loading procedure may be a consequence of stent friction interaction with the interior wall of catheter 11 while the pushing force F is applied to facilitate loading. After the loading procedure is complete, one could expect the longitudinal geometry of the stent to resiliently resume the separation distance 59 between adjacent cells 25 after the longitudinal compression is relieved.

By utilizing wide top bars 43, the individual struts 30 can be oriented parallel to the stent axis when the hollow cylindrical shape 22 is act at the tube diameter 61. This helps to permit each of the struts 30 to carry a fraction of the longitudinal loading compression in parallel with the longitudinal loading push force F. The columns 41 of the T-bars 40 can be made less stiff in the circumferential direction by material removal through the inclusion of slots 70 and 71. Thus, the slots 70 and 71 can locally reduce stiffness, allow more uniform bending, and prevent or inhibit the appearance of cracks during heat setting at an expanded diameter 62.

INDUSTRIAL APPLICABILITY

The present disclosure finds general applicability in self expanding stents. More particularly, the teachings of the present disclosure are specifically applicable to smaller diameter self expanding stents, such as those having diameters of five French or less. These smaller diameter stents might find application in, for instance, arteries in the lower leg of a patient. Although the stent 20 in the present disclosure has been illustrated in the context of being manufactured from a thin walled tube of nitinol, the present disclosure also contemplates stents made from other appropriate materials, such as biodegradable polymers that exhibit superelastic traits similar to nitinol.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A stent comprising:
    a framework having a hollow cylindrical shape with a length along a stent axis, and the framework including a sequence of cells that each occupy a discrete segment of the stent length, and each of the cells including a plurality of struts with ends connected at respective vertices;
    an adjacent pair of the cells being attached to one another by a plurality of T-bars that each include a column defining a long axis extending parallel to the stent axis and a top bar attached to one end of the column, and an opposite end of the column being attached to a first cell of the adjacent pair of cells, and the top bar being attached at opposite ends to a second cell of the adjacent pair of cells;
    the column has a minimum width perpendicular to the long axis that is wider than a maximum width of each of the struts, and the column defines at least one slot; and
    the top bar has a curved edge on a side opposite from the column and the curved edge straddles the long axis.

2. The stent of claim 1 wherein each of the struts has a width to thickness ratio about equal to one.

3. The stent of claim 1 wherein the hollow cylindrical shape is movable among a loading diameter that is smaller than a tube diameter which is smaller than an expanded diameter;
    the framework is biased toward the expanded diameter; and
    the tube diameter is 5 French or less.

4. The stent of claim 1 wherein the at least one slot is exactly two slots.

5. The stent of claim 1 wherein every strut of the framework is oriented parallel to the stent axis when the hollow cylindrical shape is at a tube diameter.

6. The stent of claim 1 wherein the sequence of cells includes at least one end cell, at least one flex cell, and at least one hoop cell; and
    the adjacent pair of cells includes exactly one flex cell and exactly one hoop cell.

7. The stent of claim 1 wherein each end of the framework terminates in exactly three eyelets.

8. The stent of claim 1 wherein adjacent cells of the sequence of cells contact each other when the framework is in a loading configuration.

9. The stent of claim 1 wherein the column has a tall H shape, with each leg of the H shape having a width that is less than a width of the struts.

10. The stent of claim 1 wherein each of the struts has a uniform width, a uniform thickness, and a rectangular cross section.

11. The stent of claim 1 wherein each adjacent pair of struts is separated by a rectangular space with a width that is less than a width of each of the adjacent pair of struts when the hollow cylindrical shape is at a tube diameter.

12. The stent of claim 1 wherein each of the vertices define a continuous inner curve with a radius that is less than one half of a width of the struts joined by a respective vertex of the vertices.

13. The stent of claim 1 wherein the curved edge is a concave edge that faces away from the column.

14. The stent of claim 1 wherein the hollow cylindrical shape is movable among a loading diameter that is smaller than a tube diameter which is smaller than an expanded diameter;
    the framework is biased toward the expanded diameter; and
    every strut of the framework is oriented parallel to the stent axis when the hollow cylindrical shape is at a tube diameter.

15. The stent of claim 14 wherein each of the struts has a width to thickness ratio about equal to one.

16. The stent of claim 14 wherein the sequence of cells includes at least one end cell, at least one flex cell, and at least one hoop cell; and
    the adjacent pair of cells includes exactly one flex cell and exactly one hoop cell.

17. The stent of claim 14 wherein each of the struts has a uniform width, a uniform thickness, and a rectangular cross section.

18. The stent of claim 1 wherein adjacent cells of the sequence of cells contact each other when the framework is in a loading configuration.

* * * * *